US009390897B2

(12) United States Patent
Castro-Perez et al.

(10) Patent No.: US 9,390,897 B2
(45) Date of Patent: *Jul. 12, 2016

(54) MASS SPECTROMETRY

(71) Applicant: Micromass UK Limited, Wilmslow (GB)

(72) Inventors: Jose M. Castro-Perez, New Providence, NJ (US); Alan Millar, Southborough, MA (US); Robert S. Plumb, Milford, MA (US)

(73) Assignee: Micromass UK Limited, Wilmslow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/492,216

(22) Filed: Sep. 22, 2014

(65) Prior Publication Data

US 2015/0008319 A1      Jan. 8, 2015

Related U.S. Application Data

(63) Continuation of application No. 13/253,312, filed on Oct. 5, 2011, now Pat. No. 8,841,606, which is a continuation of application No. 11/571,338, filed as application No. PCT/GB2005/002610 on Jul. 1, 2005, now Pat. No. 8,063,357.

(60) Provisional application No. 60/584,139, filed on Jul. 1, 2004.

(30) Foreign Application Priority Data

Jul. 5, 2004 (GB) .................................. 0415046.2

(51) Int. Cl.
*H01J 49/00* (2006.01)
*G01N 33/15* (2006.01)
(Continued)

(52) U.S. Cl.
CPC ............ *H01J 49/0031* (2013.01); *G01N 33/15* (2013.01); *G06F 19/703* (2013.01); *H01J 49/004* (2013.01); *H01J 49/26* (2013.01); *Y10T 436/24* (2015.01)

(58) Field of Classification Search
CPC ....... H01J 49/0036; H01J 49/26; H01J 49/40; H01J 49/00; H01J 49/0027; H01J 49/02; G01N 33/6848; G01N 2560/00
USPC .......... 250/281, 282; 436/173; 702/22, 27, 28
See application file for complete search history.

(56) References Cited

U.S. PATENT DOCUMENTS 4,008,388 A * 2/1977 McLafferty et al. ............ 702/27
5,072,115 A * 12/1991 Zhou ............................ 250/281
(Continued)

FOREIGN PATENT DOCUMENTS

GB          1193255         5/1970

OTHER PUBLICATIONS

Aebersold et al., "*Mass Spectrometry in Proteomics*", Chemical Reviews, vol. 101, pp. 269-295, 2001.
(Continued)

*Primary Examiner* — Michael Maskell
(74) *Attorney, Agent, or Firm* — Diederiks & Whitelaw, PLC

(57) ABSTRACT

A method of searching for potentially unknown metabolites of pharmaceutical compounds is disclosed. The accurate mass of a pharmaceutical compound will generally be known and can be rendered in the form of an integer nominal mass or mass to charge ratio component and a decimal mass or mass to charge ratio component. Possible metabolites are searched for on the basis of having a decimal mass or mass to charge ratio component which is substantially very similar to the decimal mass or mass to charge ratio of the parent pharmaceutical compound.

18 Claims, 6 Drawing Sheets

(51) Int. Cl.
  *H01J 49/26* (2006.01)
  *G06F 19/00* (2011.01)

(56) References Cited

U.S. PATENT DOCUMENTS

| | | | |
|---|---|---|---|
| 5,453,613 | A | 9/1995 | Gray et al. |
| 6,147,344 | A | 11/2000 | Annis et al. |
| 6,147,348 | A | 11/2000 | Quarmby et al. |
| 6,258,605 | B1 | 7/2001 | Chace et al. |
| 6,289,287 | B1 | 9/2001 | Meng et al. |
| 6,455,321 | B1 | 9/2002 | Chace |
| 7,291,767 | B2 | 11/2007 | Oriedo et al. |
| 7,381,568 | B2 | 6/2008 | Zhang et al. |
| 8,030,089 | B2 | 10/2011 | Geromanos et al. |
| 2002/0063208 | A1* | 5/2002 | Hastings .................. 250/281 |
| 2002/0192708 | A1 | 12/2002 | Steen et al. |
| 2003/0023386 | A1 | 1/2003 | Aranibar et al. |
| 2003/0066802 | A1 | 4/2003 | Jastoff et al. |
| 2003/0229451 | A1 | 12/2003 | Hamilton et al. |
| 2005/0164325 | A1 | 7/2005 | Leicester |
| 2005/0272168 | A1* | 12/2005 | Zhang et al. ............... 436/173 |

OTHER PUBLICATIONS

Huang et al., "*Mass Spectrometric Strategy for Primary Structure Determination of N-Terminally Blocked Peptides*", Journal of Chromatography, vol. 803, No. 1, pp. 167-172, 2004.

Karty et al., "*Artifacts and Unassigned Masses Encountered in Peptide Mass Mapping*", Journal of Chromatography Biomedical Applications, vol. 782, pp. 363-383, 2002.

Mann et al., "*In Useful Tables of Possible and Probable Peptide Masses*", American Society for Mass Spectrometry, 1995.

Schmidt et al., "*Iterative Data Analysis is the Key for Exhaustive Analysis of Peptide Mass Fingerprints from Proteins Separated by Two-Dimensional Electrophoresis*", Journal of the American Society for Mass Spectrometry, vol. 14, No. 9, pp. 943-956, 2003.

Zhang et al., "*A Software Filter to Remove Interference Ions From Drug Metabolites in Accurate Mass Liquid Chromatography/Mass Spectrometric Analyses*", Journal of Mass Spectrometry, vol. 38, pp. 1110-1112, 2003.

Zhang et al.,"*MSPurift: Leveraging High Resolution LC/MS Data to Identify Drug Metabolite Ions in Samples of Human Excreta*" Journal of the ASMS, 2003.

* cited by examiner

MASS SPECTROMETRY

CROSS REFERENCE TO RELATED APPLICATIONS

This application is a continuation of U.S. application Ser. No. 13/253,312, filed Oct. 5, 2011, which is a continuation of U.S. application Ser. No. 11/571,338, filed Sep. 15, 2008, which is the National Stage of International Application No. PCT/GB2005/002610, filed on Jul. 1, 2005, which claims priority to and benefit of U.S. Provisional Patent Application Ser. No. 60/584,139, filed on Jul. 1, 2004, and priority to and benefit on United Kingdom Patent Application No. 0415406, filed Jul. 5, 2004. The entire contents of these applications are incorporated herein by reference.

BACKGROUND OF THE PRESENT INVENTION

The present invention relates to a mass spectrometer and a method of mass spectrometry.

In drug metabolism studies metabolites of interest cannot usually be predicted. This is because the formation of metabolites may be determined by novel enzymatic reactions and by factors which are difficult to predict in advance such as bio-availability.

At present in order to detect and identify metabolites it is known to separate out the many different components present, in a complex biological matrix using liquid chromatography (LC or HPLC). The mass or mass to charge ratio of the components eluting from the liquid chromatograph is then measured using mass spectrometry (MS).

It is usually necessary to make many measurements using LC-MS. (wherein parent, ions eluting from a liquid chromatograph are mass analysed) and LC-MS-MS (wherein specific parent ions eluting from a liquid chromatograph are fragmented and the fragment products are mass analysed) often in both positive and negative ionisation modes. The exact accurate mass or mass to charge ratio of the components eluting from the liquid chromatograph is normally determined since this enables many of the large number of endogenous peaks present in different biological matrices such as bile, plasma, faeces and urine to be discounted.

Ions which are determined as having a mass to charge ratio which indicates that they may relate to a metabolite of interest are then fragmented in a collision cell. The resulting fragment products are then mass analysed enabling the structure of each possible metabolite to be predicted.

The conventional approach is, however, relatively time consuming since it is necessary to interrogate all of the mass spectral data to look for potential metabolites of interest. It is then necessary to arrange for all ions which are considered likely to relate to metabolites of interest then to be separately fragmented so that the structure of potential metabolites of interest can then be determined.

It will be appreciated that the process of searching mass spectra relating to a complex mixture, identifying potential ions which may relate to metabolites of interest, selecting certain ions to be fragmented, fragmenting the ions of interest and then mass analysing the fragment products can be relatively time consuming.

Within the pharmaceutical and biotechnology industries it is particularly important to be able to analyse samples quickly and accurately. This has led to automated methods wherein the major peaks present in a mass spectrum are automatically selected for analysis by MS/MS (wherein specific parent ions are selected for fragmentation). This allows the user to acquire parent ion mass spectra and several MS/MS spectra from a single HPLC injection. It is known for to automatically select most intense peaks (i.e. ions) in a parent ion mass spectrum for subsequent analysis by MS/MS. Some conventional systems allow a few filters to be defined to make this process slightly more efficient. For example, ions having certain masses or mass to charge ratios may be entered into a data system so that, they are automatically excluded from consideration. These masses or mass to charge ratios may, for example, correspond to the masses or mass to charge ratios of solvent peaks which are known to be present, or the masses or mass to charge ratios of components which have already been analysed.

An advantage of the conventional automated mode of data acquisition is that a fair degree of data may be acquired from a single HPLC injection. However, a disadvantage of the conventional approach is that only chose peaks which have an intensity which exceeds a pre-defined intensity threshold are normally selected for subsequent MS/MS analysis (i.e. fragmentation analysis). Importantly, if a large number of intense peaks are present or observed at any one particular time, then some of these peaks may simply fail to be selected for MS/MS analysis due to there being insufficient time to record all the separate MS/MS spectra within the relatively short duration of an observed chromatography peak.

Another particular problem with the conventional approach is that since the mass or mass to charge ratios of potential metabolites is not generally known in advance, then time can be wasted analysing a large number of peaks all or many of which subsequently turn out to be of little or no interest. This can also mean that actual peaks of potential interest which could have been analysed if only they had been recognised fail to be analysed at all because the mass spectrometer is busy analysing other ions.

It is therefore desired to provide an improved method of mass spectrometry and in particular to improve upon the current approach of searching for metabolites of interest.

SUMMARY OF THE PRESENT INVENTION

According to an aspect of the present, invention there is provided a method of mass spectrometry comprising:

determining the accurate or exact, mass or mass to charge ratio of a first substance or ion, wherein the accurate or exact mass or mass to charge ratio comprises a first integer nominal mass or mass to charge ratio component and a first decimal mass or mass to charge ratio component; and searching for one or more second substances or ions having a decimal mass or mass to charge ratio component which is between 0 to $x_1$ mDa or milli-mass to charge ratio units greater than the first decimal mass or mass to charge ratio component and/or between 0 to $x_2$ mDa or milli-mass to charge ratio units lesser than the first decimal mass or mass to charge ratio component.

The step of searching for one or more second substances or ions preferably comprises searching solely on the basis of the decimal mass or mass to charge ratio component of the one or more second substances or ions and not on the basis of the integer nominal mass or mass to charge ratio component of the one or more second substances or ions.

The step of searching for one or more second substances or ions preferably comprises searching some or all second substances or ions which have an integer nominal mass or mass to charge ratio component which is different, from the first integer nominal mass or mass to charge ratio component.

According to an embodiment $x_1$ falls within a range selected from the group consisting of: (i) <1; (ii) 1-5; (iii) 5-10; (iv) 10-15; (v) 15-20; (vi) 20-25; (vii) 25-30; (viii)

30-35; (ix) 35-40; (x) 40-45; (xi) 45-50; (xii) 50-55; (xiii) 55-60; (xiv) 60-65; (xv) 65-70; (xvi) 70-75; (xvii) 75-80; (xviii) 80-85; (xix) 85-90; (xx) 90-95; (xxi) 95-100; and (xxii) >100. Similarly, $x_2$ preferably falls within a range selected from the group consisting of: (i) <1; (ii) 1-5; (iii) 5-10; (iv) 10-15; (v) 15-20; (vi) 20-25; (vii) 25-30; (viii) 30-35; (ix) 35-40; (x) 40-45; (xi) 45-50; (xii) 50-55; (xiii) 55-60; (xiv) 60-65; (xv) 65-70; (xvi) 70-75; (xvii) 75-80; (xviii) 80-85; (xix) 85-90; (xx) 90-95; (xxi) 95-100; and (xxii) >100.

According to an embodiment the first substance or ion comprises or relates to a pharmaceutical compound, drug or active component. Preferably, the one or more second substances or ions comprise or relate to one or more metabolites or derivatives of the first substance or ion.

According to an embodiment the first substance or ion comprises a biopolymer, protein, peptide, polypeptide, oligionucleotide, oligionucleoside, amino acid, carbohydrate, sugar, lipid, fatty acid, vitamin, hormone, portion or fragment, of DNA, portion or fragment of cDNA, portion or fragment of RNA, portion or fragment of mRNA, portion or fragment of tRNA, polyclonal antibody, monoclonal antibody, ribonuclease, enzyme, metabolite, polysaccharide, phosphorolated peptide, phosphorolated protein, glycopeptide, glycoprotein or steroid. Similarly, according to an embodiment the one or more second substance or ion comprises a biopolymer, protein, peptide, polypeptide, oligonucleotide, oligionucleoside, amino acid, carbohydrate, sugar, lipid, fatty acid, vitamin, hormone, portion or fragment of DNA, portion or fragment of cDNA, portion or fragment of RNA, portion or fragment of mRNA, portion or fragment of tRNA, polyclonal antibody, monoclonal antibody, ribonuclease, enzyme, metabolite, polysaccharide, phosphorolated peptide, phosphorolated protein, glycopeptide, glycoprotein or steroid.

The sample to be analysed preferably comprises at least 2, 5, 10, 20, 30, 40, 50, 60, 70, 80, 90, 100, 200, 300, 400, 500, 600, 700, 800, 900, 1000, 1500, 2000, 2500, 3000, 3500, 4000, 4500, or 5000 components, molecules or analytes having different identities or comprising different species.

The step of searching for one or more second substances or ions preferably further comprises applying a decimal mass or mass to charge ratio window to mass spectral data or a mass spectrum. The decimal mass or mass to charge ratio window preferably filters out, removes, attenuates or at least reduces the significance of second substances or ions having a decimal mass or mass to charge ratio component which falls outside of the decimal mass or mass to charge ratio window.

The accurate or exact mass or mass to charge ratio of the first substance or ion minus the accurate or exact mass or mass to charge ratio of a second substance or ion preferably has a value of $\Delta M$ Daltons or mass to charge ratio units. According to an embodiment $x_1$ and/or $x_2$ may vary as a function of $\Delta M$ in a symmetrical manner. For example, $x_1$ and/or $x_2$ may vary as a function of $\Delta M$ in a symmetrical manner about a value of $\Delta M$ selected from the group consisting of: (i) 0; (ii) ±0-5; (iii) ±5-10; (iv) ±10-15; (v) ±15-20; (vi) ±20-25; (vii) ±25-30; (viii) ±30-35; (ix) ±35-40; (x) ±40-45; (xi) ±45-50; (xii) ±50-55; (xiii) ±55-60; (xiv) ±60-65; (xv) ±65-70; (xvi) ±70-75; (xvii) ±75-80; (xviii) ±80-85; (xix) ±85-90; (xx) ±90-95; (xxi) ±95-100; (xxii) >100; and (xxiii) <-100.

According to the preferred embodiment $x_1$ and/or $x_2$ may vary as a function of $\Delta M$ in an asymmetrical manner. Preferably, if $M_{lower} < \Delta M$ and/or $\Delta M < M_{upper}$ then $x_1$ and/or $x_2$ has a substantially constant value. Preferably, if $M_{lower} > \Delta M$ and/or $\Delta M > M_{upper}$ then $x_1$ and/or $x_2$ has a substantially non-constant value as a function of $\Delta M$. If $M_{lower} > \Delta M$ and/or $\Delta M > M_{upper}$ then $x_1$ and/or $x_2$ preferably varies in a substantially linear manner as a function of $\Delta M$. According to an embodiment over at least a range of $\Delta M$ values, $x_1$ and/or $x_2$ preferably increases or decreases at a rate of y %*$\Delta M$, wherein y is selected from the group consisting of: (i) <0.01; (ii) 0.01-0.02; (iii) 0.02-0.03; (iv) 0.03-0.04; (v) 0.04-0.05; (vi) 0.05-0.06; (viii) 0.06-0.07; (ix) 0.07-0.08; (x) 0.08-0.09; (xi) 0.09-0.10; (xii) 0.10-0.11; (xiii) 0.11-0.12; (xiv) 0.12-0.13; (xv) 0.13-0.14; (xvi) 0.14-0.15; (xvii) 0.15-0.16; (xviii) 0.16-0.17; (xix) 0.17-0.18; (xx) 0.18-0.19; (xxi) 0.19-0.20; and (xxii) >0.20.

According to an embodiment if $M_{lower} > \Delta M$ and/or $\Delta M > M_{upper}$ then $x_1$ and/or $x_2$ varies in a substantially curved, stepped or non-linear manner as a function of $\Delta M$.

Preferably, $M_{upper}$ is a value in Daltons or mass to charge ratio units and falls within a range selected from the group consisting of: (i) <1; (ii) 1-5; (iii) 5-10; (iv) 10-15; (v) 15-20; (vi) 20-25; (vii) 25-30; (viii) 30-35; (ix) 35-40; (x) 40-45; (xi) 45-50; (xii) 50-55; (xiii) 55-60; (xiv) 60-65; (xv) 65-70; (xvi) 70-75; (xvii) 75-80; (xviii) 80-85; (xix) 85-90; (xx) 90-95; (xxi) 95-100; and (xxii) >100. Similarly, $M_{lower}$ is preferably a value in Daltons or mass to charge ratio units and falls within a range selected from the group consisting of: (i) <-100; (ii) -100 to -95; (iii) -95 to -90; (iv) -90 to -85; (v) -85 to -80; (vi) -80 to -75; (vii) -75 to -70; (viii) -70 to -65; (ix) -65 to -60; (x) -60 to -55; (xi) -55 to -50, (xii) -50 to -45; (xiii) -45 to -40; (xiv) -40 to -35; (xv) -35 to -30; (xvi) -30 to -25; (xvii) -25 to -20; (xviii) -20 to -15; (xix) -15 to -10; (xx) -10 to -5; (xxi) -5 to -1; and (xxii) >-1.

According to an embodiment the method further comprises selecting for further analysis one or more second substances or ions which have a decimal mass or mass to charge ratio component which is between 0 to $x_1$ mDa or milli-mass to charge ratio units greater than the first decimal mass or mass to charge ratio component and/or between 0 to $x_2$ mDa or milli-mass to charge ratio units lesser than the first decimal mass or mass to charge ratio component. Preferably, the step of selecting for further analysis comprises fragmenting the one or more second substances or ions.

The step of selecting for further analysis preferably comprises onwardly transmitting one or more second substances or ions which have a decimal mass or mass to charge ratio component which is between 0 to $x_1$ mDa or milli-mass to charge ratio units greater than the first decimal mass or mass to charge ratio component and/or between 0 to $x_2$ mDa or milli-mass to charge ratio units lesser than the first decimal mass or mass to charge ratio component to a collision or fragmentation cell. According to an embodiment the method further comprises mass analysing the fragment products or ions which result from fragmenting the one or more second substances or ions.

According to an embodiment the method further comprises separating components, analytes or molecules in a sample to be analysed by means of a separation process. Preferably, the separation process comprises liquid chromatography. According to an embodiment the separation process may comprise: (i) High Performance Liquid Chromatography ("HPLC"); (ii) anion exchange, (iii) anion exchange chromatography; (iv) cation exchange; (v) cation exchange chromatography; (vi) ion pair reversed-phase chromatography; (vii) chromatography; (viii) single dimensional electrophoresis; (ix) multi-dimensional electrophoresis; (x) size exclusion; (xi) affinity; (xii) reverse phase chromatography; (xiii) Capillary Electrophoresis Chromatography ("CEC"); (xiv) electrophoresis; (xv) ion mobility separation; (xvi) Field Asymmetric Ion Mobility Separation or Spectrometry ("FAIMS");

(xvii) capillary electrophoresis; (xviii) gas chromatography; and (xix) supercritical fluid chromatography.

According to an embodiment the method preferably further comprises ionising components, analytes or molecules in a sample to be analysed. The ion source may comprise a pulsed ion source or a continuous ion source. According to an embodiment the ion source may be selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; and (xvi) a Nickel-63 radioactive ion source.

According to an embodiment the method further comprises mass analysing the first substance or ion and/or the one or more second substances or ions and/or fragment products or ions using a mass analyser. The mass analyser preferably comprises a quadrupole mass analyser. According to other embodiments the mass analyser may comprise a mass analyser selected from the group consisting of: (i) a Fourier Transform ("FT") mass analyser; (ii) a Fourier Transform Ion Cyclotron Resonance ("FTICR") mass analyser; (iii) a Time of Flight ("TOF") mass analyser; (iv) an orthogonal acceleration Time of Flight ("oaTOF") mass analyser; (v) an axial acceleration Time of Flight mass analyser; (vi) a magnetic sector mass spectrometer; (vii) a Paul or 3D quadrupole mass analyser; (viii) a 2D or linear quadrupole mass analyser; (ix) a Penning trap mass analyser; (x) an ion trap mass analyser; (xi) a Fourier Transform orbitrap; (xii) an electrostatic Ion Cyclotron Resonance mass spectrometer; and (xiii) an electrostatic Fourier Transform mass spectrometer.

The exact or accurate mass or mass to charge ratio of the first substance or ion and/or the one or more second substances or ions is preferably determined to within 20 ppm, 19 ppm, 18 ppm, 17 ppm, 16 ppm, 15 ppm, 14 ppm, 13 ppm, 12 ppm, 11 ppm, 10 ppm, 9 ppm, 8 ppm, 7 ppm, 6 ppm, 5 ppm, 4 ppm, 3 ppm, 2 ppm, 1 ppm or <1 ppm.

The exact or accurate mass or mass to charge ratio of the first substance or ion and/or the one or more second substances or ions is preferably determined to within 0.01 mass units, 0.009 mass units, 0.008 mass units, 0.007 mass units, 0.006 mass units, 0.005 mass units, 0.004 mass units, 0.003 mass units, 0.002 mass units, 0.001 mass units or <0.001 mass units.

The sample which is analysed according to the preferred embodiment is preferably taken from a diseased organism, a non-diseased organism, a treated organism, a non-treated organism, a mutant organism or a wild type organism.

According to an embodiment the method preferably further comprises identifying or determining the composition of one or more of the second substances or ions.

According to an embodiment the method further comprises quantifying or determining the intensity, concentration or expression level of the first substance or ions. Preferably, the method further comprises quantifying or determining the intensity, concentration or expression level of one or more of the second substances or ions.

The method preferably further comprises determining or quantifying the relative intensity, concentration or expression level of one or more of the first substances or ions. Preferably, the method further comprises determining or quantifying the relative intensity, concentration or expression level of one or more of the second substances or ions.

According to an aspect of the present invention there is provided a method of mass spectrometry comprising:

determining the accurate mass to charge ratio of a parent ion, wherein the accurate mass to charge ratio comprises a first integer value and a first decimal value;

searching for one or more metabolites of the parent ion, wherein the step of searching comprises;

(i) determining the accurate mass to charge ratio of ions of potential interest, wherein the accurate mass to charge ratio of each of the ions of potential interest comprises a second integer value and a second decimal value; and (ii) recognising, selecting, preferentially mass filtering or transmitting, determining or fragmenting ions amongst the ions of potential interest on the basis of the ions having an accurate mass to charge ratio wherein the second decimal value is within x mDa or milli-mass to charge ratio units of the first decimal value.

Preferably, x falls within a range selected from the group consisting of: (i) <1; (ii) 1-5; (iii) 5-10; (iv) 10-15; (v) 15-20; (vi) 20-25; (vii) 25-30; (viii) 30-35; (ix) 35-40; (x) 40-45; (xi) 45-50; (xii) 50-55; (xiii) 55-60; (xiv) 60-65; (xv) 65-70; (xvi) 70-75; (xvii) 75-80; (xviii) 80-85; (xix) 85-90; (xx) 90-95; (xxi) 95-100; and (xxii) >100.

According to an aspect of the present invention there is provided a mass spectrometer comprising:

means arranged and adapted to determine the accurate mass to charge ratio of a parent ion, wherein the accurate mass to charge ratio comprises a first integer value and a first decimal value;

means arranged and adapted to search for one or more metabolites of the parent ion, wherein the means is arranged and adapted to:

(i) determine the accurate mass to charge ratio of ions of potential interest, wherein the accurate mass to charge ratio of each of the ions of potential interest comprises a second integer value and a second decimal value; and (ii) recognise, select, preferentially mass filter or transmit, determine or fragment ions amongst, the Ions of potential interest on the basis of the ions having accurate mass to charge ratio wherein the second decimal value is within x mDa or milli-mass to charge ratio units of the first decimal value.

According to the preferred embodiment x falls within a range selected from the group consisting of: (i) <1; (ii) 1-5; (iii) 5-10; (iv) 10-15; (v) 15-20; (vi) 20-25; (vii) 25-30; (viii) 30-35; (ix) 35-40; (x) 40-45; (xi) 45-50; (xii) 50-55; (xiii) 55-60; (xiv) 60-65; (xv) 65-70; (xvi) 70-75; (xvii) 75-80; (xviii) 80-85; (xix) 85-90; (xx) 90-95; (xxi) 95-100; and (xxii) >100.

According to an aspect of the present invention there is provided a mass spectrometer comprising:

means arranged and adapted to determine the accurate or exact mass or mass to charge ratio of a first substance or ion, wherein the accurate or exact mass or mass to charge ratio comprises a first integer nominal mass or mass to charge ratio component and a first decimal mass or mass to charge ratio component; and a processing device arranged and adapted to search for one or more second substances or ions having a decimal mass or mass to charge ratio component which is between 0 to $x_1$ mDa or milli-mass to charge ratio units greater than the first decimal mass or mass to charge ratio component and/or between 0 to $x_2$ mDa or milli-mass to charge ratio units lesser than the first decimal mass or mass to charge ratio component.

According to an aspect of the present invention there is provided a method of mass spectrometry comprising searching for potential metabolites of a parent drug on the basis of the metabolites having substantially similar decimal mass or mass to charge ratios to that of the parent drug.

The step of searching preferably further comprises: fragmenting ions relating to a potential metabolite of a parent drug so that a plurality of fragment ions are produced; and mass analysing the fragment ions.

According to an aspect of the present invention there is provided a mass spectrometer comprising a processing device arranged and adapted to search for potential metabolites of a parent drug, wherein the means searches for ions having substantially similar decimal mass or mass to charge ratios to that of the parent drug.

The mass spectrometer preferably further comprises: means for fragmenting ions relating to a potential metabolite of a parent drug so that a plurality of fragment ions are produced; and means for mass analysing the fragment ions.

According to an aspect of the present invention there is provided a method of mass spectrometry comprising:
applying a decimal mass or mass to charge ratio window to mass spectral data or a mass spectrum;
determining ions having a decimal mass or mass to charge ratio which falls within the decimal mass or mass to charge ratio window;
fragmenting at least some of the ions which have a decimal mass or mass to charge ratio which falls within the decimal mass or mass to charge ratio window to produce a plurality of fragment ions; and
mass analysing at least some of the plurality of fragment ions.

The decimal mass or mass to charge ratio window preferably has a profile which varies as a function of $\Delta M$, wherein $\Delta M$ is the difference in mass or mass to charge ratio between a first substance or ion and a second substance or ion.

The first substance or ion preferably comprises a pharmaceutical compound and the second substance or ion comprises a metabolite of the first substance or ion.

According to an aspect of the present invention there is provided a mass spectrometer comprising:
means arranged and adapted to apply a decimal mass or mass to charge ratio window to mass spectral data or a mass spectrum;
means arranged and adapted to determine ions having a decimal mass or mass to charge ratio which falls within the decimal mass or mass to charge ratio window;
means arranged and adapted to fragment at least some of the ions which have a decimal mass or mass to charge ratio which falls within the decimal mass or mass to charge ratio window to produce a plurality of fragment ions; and
means arranged and adapted to mass analyse at least some of the plurality of fragment ions.

According to an aspect of the present invention there is provided a method of mass spectrometry comprising:
providing a biological sample which includes one of metabolites of a pharmaceutical compound;
subjecting the sample to liquid chromatography;
ionising the eluent emerging from a liquid chromatograph to produce a plurality of ions;
mass analysing the ions; and
determining whether one or more of the ions have a mass or mass to charge ratio which has a decimal mass or mass to charge ratio component which is within x mDa or milli-mass to charge ratio units of the decimal mass or mass to charge ratio of the pharmaceutical compound.

Preferably, x is selected from the group consisting of: (i) 1; (ii) 2; (iii) 3; (iv) 4; (v) 5; (vi) 6; (vii) 7; (viii) 8; (ix) 9; (x) 10; (xi) 11; (xii) 12; (xiii) 13; (xiv) 14; (xv) 15; (xvi) 16; (xvii) 17; (xviii) 18; (xix) 19; (xx) 20; (xxi) 21; (xxii) 22; (xxiii) 23; (xxiv) 24; (xxv) 25; (xxvi) 26; (xxvii) 27; (xxviii) 28; (xxix) 29; (xxx) 30; (xxxi) 31; (xxxii) 32; (xxxiii) 33; (xxxiv) 34; (xxxv) 35; (xxxvi) 36; (xxxvii) 37; (xxxviii) 38; (xxxix) 39; (xl) 40; and (xli) >40.

According to an aspect of the present invention there is provided a mass spectrometer comprising:
a liquid chromatograph arranged to subject, in use, a biological sample which includes one of metabolites of a pharmaceutical compound to liquid chromatography;
an ion source for ionising the eluent emerging from the liquid chromatograph to produce a plurality of ions;
a mass analyser for mass analysing the ions; and
means arranged and adapted to determine whether one or more of the ions have a mass or mass to charge ratio which has a decimal mass or mass to charge ratio component which is within x mDa or milli-mass to charge ratio units of the decimal mass or mass to charge ratio of the pharmaceutical compound.

Preferably, x is selected from the group consisting of: (i) 1; (ii) 2; (iii) 3; (iv) 4; (v) 5; (vi) 6; (vii) 7; (viii) 8; (ix) 9; (x) 10; (xi) 11; (xii) 12; (xiii) 13; (xiv) 14; (xv) 15; (xvi) 16; (xvii) 17; (xviii) 18; (xix) 19; (xx) 20; (xxi) 21; (xxii) 22; (xxiii) 23; (xxiv) 24; (xxv) 25; (xxvi) 26; (xxvii) 27; (xxviii) 28; (xxix) 29; (xxx) 30; (xxxi) 31; (xxxii) 32; (xxxiii) 33; (xxxiv) 34; (xxxv) 35; (xxxvi) 36; (xxxvii) 37; (xxxviii) 38; (xxxix) 39; (xi) 40; and (xii) >40.

An advantage of the preferred embodiment is that potentially only drug related metabolite peaks are selected for subsequent analysis by MS/MS and that ail or at least a majority of the endogenous peaks are effectively ignored from further consideration. The preferred embodiment therefore significantly improves the process of searching for and mass analysing ions relating to metabolites of interest. The preferred embodiment also enables metabolites of interest to be selected for further analysis by, for example, fragmenting them within the inherent short timescales of liquid chromatography.

The preferred embodiment, in effect, filters out or substantially removes from consideration a number of possible precursor ions for subsequent analysis by MS/MS in drug metabolism studies by selecting only those ions which have a mass or mass to charge ratio wherein the decimal part of the mass or mass to charge ratio falls within a pre-defined and preferably relatively narrow decimal mass or mass to charge ratio window.

BRIEF DESCRIPTION OF THE DRAWINGS

Various embodiments of the present invention will now be described, by way of example only, and with reference to the accompanying drawings in which.

DETAILED DESCRIPTION OF THE PREFERRED EMBODIMENTS

Figure 1:
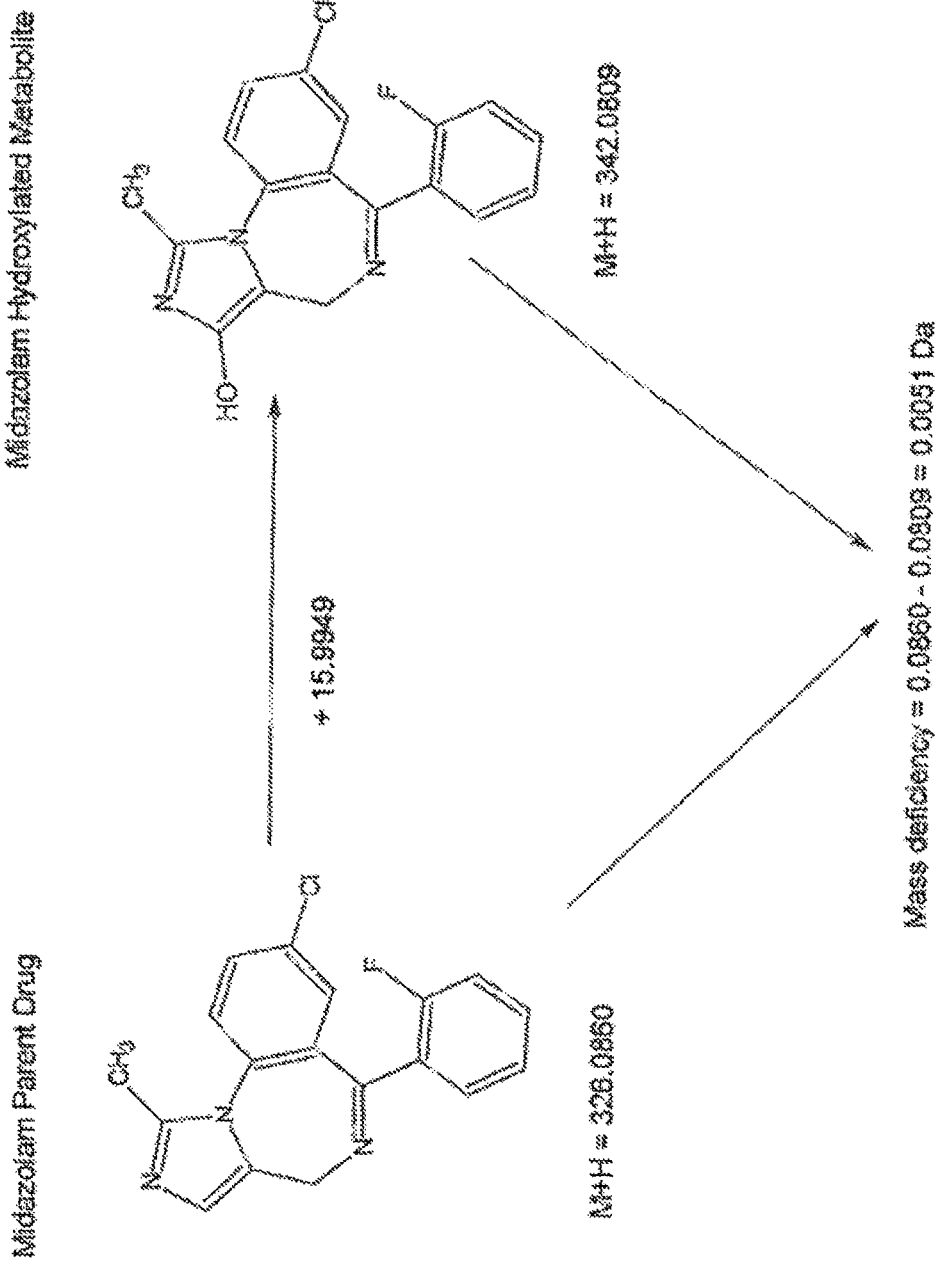
FIG. 1 shows the structure and exact mass of a parent drug called Midazolam and the structure and exact mass of a hydroxylated metabolite of Midazolam.

In metabolism studies the elemental composition of a parent drug is usually generally well known and hence it is possible to calculate the theoretical exact mass or mass to charge ratio of the parent drug. An example of a pharmaceutical drug and a related metabolite which may be recognised (and hence selected for further analysis) according to the preferred embodiment is shown in FIG. 1. FIG. 1 shows the elemental composition of a parent drug called Midazolam ($C_{18}H_{13}ClFN_3$) which has a monoisotopic protonated mass of 326.0860 Da. A common metabolic route for the drug is the addition of oxygen. Accordingly, if an oxygen is added to Midazolam then the mass will be increased by +15.9949 Da so that the monoisotopic mass of the new compound (i.e. the hydroxylated metabolite of Midazolem) will be 342.0809 Da.

The structure of the hydroxylated metabolite of Midazolem is also shown in FIG. 1. It is to be noted that the difference in the decimal part of the accurate mass of the parent drug Midaszolem and its hydroxylated metabolite is only 0.0860−0.0809=0.0051 Da (i.e. a mass deficiency of only 5.1 mDa). It is apparent therefore that there is only a very small difference in the decimal mass component of the parent drug and the corresponding metabolite even though the total or absolute mass of the parent and metabolite differ by nearly 16 Da.

In mass spectrometry an ion may be assigned either an integer nominal mass or mass to charge ratio (e.g. 326 in the case of Midazolam) or an accurate or exact mass or mass to charge ratio (e.g. 326.0860 in the case of Midazolam). Accurate or exact masses or mass to charge ratios can be considered as comprising an integer component or value and a decimal component or value. This largely stems from the fact that all the elements (with the exception of Carbon) have approximately but not exactly integer masses. In the international scale for atomic masses the most abundant isotope of carbon is assigned an exact atomic mass of 12.0000 Dalton (Da). On this scale, the accurate atomic masses of the most abundant isotopes of the most abundant elements in biological systems are Hydrogen (H) 1.0078 Da, Nitrogen (N) 14.0031 Da and Oxygen (O) 15.9949 Da.

Accurate or exact (i.e. non-integer) masses or mass to charge ratios can be represented as an integer nominal mass or mass to charge ratio value or component together with a corresponding mass sufficiency or deficiency value or component. The mass sufficiency or deficiency may be considered to represent the deviation from an integer value and may be expressed in milli-dalton (mDa). For example, Hydrogen (H) can be expressed as having an integer nominal mass of 1 and a mass sufficiency of 7.8 mDa, Nitrogen (N) can be expressed as having an integer nominal mass of 14 and a mass sufficiency of 3.1 mDa and Oxygen (O) can be expressed as having an integer nominal mass of 16 and a mass deficiency of 5.1 mDa.

In a similar manner, the mass or mass to charge ratio of an ion of an organic molecule can be assigned an integer nominal mass or mass to charge ratio together with a corresponding mass sufficiency or deficiency from that integer value.

When considering the mass or mass to charge ratio of ions or compounds according to the preferred embodiment, the method of ionisation is also preferably taken into consideration as this allows the ionic elemental composition to be determined and hence also the ionic mass or mass to charge ratio to be calculated. For example, if a solution Is ionised by Electrospray ionisation then the analyte molecules may be protonated to form positively charged ions.

From knowledge of the theoretical accurate mass or mass to charge ratio of these ions it is possible, according to the preferred embodiment, to make certain predictions concerning the accurate mass or mass to charge ratio of possible or potential metabolites of interest. This in turn allows a better prediction of peaks that are likely to be metabolites of interest and thus potential metabolites can be searched for, recognised and then passed or selected for further analysis such as structural analysis by MS/MS.

Metabolites are the result of bio-transformations to a parent drug. An aspect of the preferred embodiment is the recognition and exploitation of the fact that the mass sufficiency or mass deficiency of a potential metabolite of interest will be substantially similar to the mass sufficiency or mass deficiency of the corresponding parent drug.

An aspect of the preferred embodiment is the recognition that the potential similarity between the mass sufficiency or mass deficiency of the parent ion and potential metabolites can be used to search more strategically for potential metabolites of interest. In particular, the preferred embodiment searches for metabolites on the basis that the decimal part of the accurate or exact mass or mass to charge ratio of a parent drug will be substantially similar to the decimal part of the accurate or exact mass or mass to charge ratio of a metabolite of the parent drug.

According to the preferred embodiment the decimal part of the accurate mass or mass to charge ratio of a precursor ion of a parent drug is calculated. A decimal mass or mass to charge ratio window is then preferably set about the precise decimal mass or mass to charge ratio of the parent drug. According to the preferred embodiment an upper limit and a lower limit to the decimal mass window may be set. However, according to other embodiments only an upper limit or only a lower limit to the decimal mass window may be set. According to an embodiment the upper and lower limits may have the same magnitude or width, or alternatively the upper and lower limits may differ in magnitude or width.

According to a preferred embodiment a precursor or parent ion mass spectrum of a sample believed to contain one or more metabolites of interest is preferably obtained. The parent ion mass spectrum is then preferably automatically searched for some or all mass peaks which meet the criteria that the decimal part of the accurate mass or mass to charge ratio of an ion must be very close to the decimal mass part of the accurate mass or mass to charge ratio of the known parent compound or ion. According to the preferred embodiment ions of potential interest (which preferably relate to one or more metabolites of the parent compound) are recognised, identified or otherwise selected for further analysis by virtue of the fact that the decimal, mass or mass to charge ratio of the ion is determined as falling within a relatively narrow band or range of masses or mass to charge ratios about the decimal mass or mass to charge ratio of the parent compound or ion.

The characteristics of the decimal mass or mass to charge ratio window which is preferably used in the process of searching for metabolites of interest will now be described in more detail with reference to FIG. 2.

Figure 2:
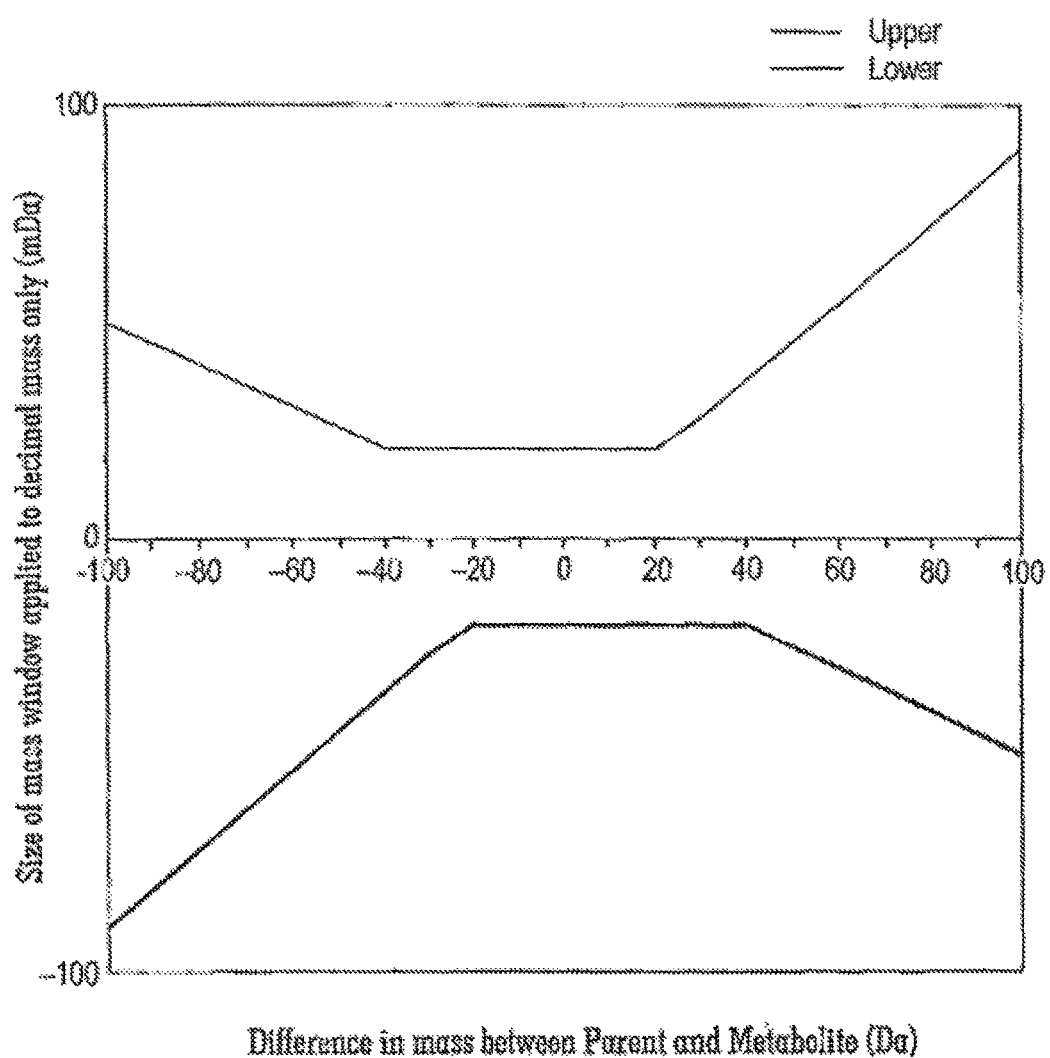
FIG. 2 indicates the upper and lower limits of a decimal mass or mass to charge ratio window according to the preferred embodiment which is applied to the decimal mass or mass to charge ratio value of ions when searching mass spectral data or a mass spectrum for metabolites of a parent drug.

FIG. 2 indicates the width of a decimal mass or mass to charge ratio window which may be used or applied according to the preferred embodiment. The width of the decimal mass or mass to charge ratio window (in mDa) is shown as a function of the difference in the absolute mass (in Da) or mass to charge ratio between that of the parent ion or compound and ions or compounds being searched for which may include metabolite ions or compounds. The difference in absolute mass or mass to charge ratio between the parent compound or ion and the ions or compounds being searched for, which may include metabolite ions or compounds of interest, may be referred to as $\Delta M$. Similarly, the upper and lower limits of the decimal mass or mass to charge ratio window may be referred to as having a value $\delta m$.

By way of example, if the absolute difference in mass or mass to charge ratio between the parent ion and a potential ion of interest is 10 Da then according to the embodiment shown in FIG. 2 a decimal mass or mass to charge ratio window having an upper limit +20 mDa greater than the precise decimal, mass or mass to charge ratio of the parent ion and a lower limit 20 mDa below the precise decimal mass or mass to charge ratio of the parent ion may be set.

According to the preferred embodiment, the upper and lower limits of the decimal mass or mass to charge ratio window vary as a function of the absolute difference $\Delta M$ in the mass or mass to charge ratio of the parent ion to that of a possible metabolite ion. Therefore, as also shown in FIG. 2, if the absolute difference in mass or mass to charge ratio between the parent ion and a potential, ion of interest is say 100 Da, then according to the embodiment shown and described with reference to FIG. 2 the upper and lower limits of the decimal mass or mass to charge ratio window are asymmetric. According to the particular embodiment shown in FIG. 2 the mass or mass to charge ratio window has an upper limit +92 mDa greater than the precise decimal mass or mass to charge ratio of the parent ion and a lower limit only 50 mDa lesser than the precise decimal mass or mass to charge ratio of the parent ion.

In general terms and as shown in FIG. 2, when the difference $\Delta M$ in mass or mass to charge ratio between the parent ion or compound and the metabolite ion or compound of interest is relatively small (e.g. ±0-30 Da) then the size of the upper and lower limits of the decimal mass or mass to charge ratio window according to the preferred embodiment may also be relatively small (e.g. in the region of 20-30 mDa). However, as the absolute difference $\Delta M$ in the mass or mass to charge ratio between the parent ion or compound and a possible metabolite ion or compound of interest increases, then so the size of the upper and lower limits of the decimal mass or mass to charge ratio window also preferably increases.

According to the embodiment shown in FIG. 2, when searching for metabolites of interest wherein the mass or mass to charge ratio difference $\Delta M$ (i.e. the mass or mass to charge ratio of the parent ion or compound, minus the mass or mass to charge ratio of the metabolite ion or compound) is in the range −40 to 20 Da, then the upper limit of the decimal mass or mass to charge ratio window is preferably set to a constant value of 20 mDa. If the mass or mass to charge, ratio difference between the parent ion or compound and the metabolite ion or compound of interest is >20 Da, then the upper limit of the decimal mass or mass to charge ratio window preferably increases at a rate of +0.09% times $\Delta M$ above 20 Da (i.e. when $\Delta M$ is +100, then the upper limit of the decimal mass window or mass to charge ratio is preferably set at 20 mDa+0.09%*(100 Da−20 Da)=20 mDa+0.072 Da=92 mDa). If the mass or mass to charge ratio difference between the parent ion or compound and the metabolite ion or compound of interest is <−40 Da, then the upper limit of the decimal mass or mass to charge ratio window preferably increases at a lesser rate of 0.05% times $\Delta M$ below −40 Da (i.e. when $\Delta M$ is −100, then the upper limit of the decimal mass or mass to charge ratio window is set at 20 mDa + 0.05%*(100 Da−40 Da)=20 mDa+0.03 Da=50 mDa).

Similarly, when searching for metabolites of interest wherein the mass or mass to charge ratio difference $\Delta M$ between the parent ion or compound, and the metabolite ion or compound is in the range −20 to 40 Da, then the lower limit of the decimal mass or mass to charge ratio window is preferably set to a constant value of −20 mDa. If the mass or mass to charge ratio difference between the parent, ion or compound and the metabolite ion or compound of interest is >40 Da, then the lower limit of the decimal mass or mass to charge ratio window preferably increases negatively at a rate of −0.05% times $\Delta M$ above 40 Da (i.e. when $\Delta M$ is +100, then the lower limit of the decimal mass or mass to charge ratio window is preferably set at −20 mDa−0.05%*(100 Da−40 Da)=−20 mDa−0.030 Da=−50 mDa). If the mass or mass to charge ratio difference between the parent ion or compound and the metabolite ion or compound of interest is <−20 Da, then the lower limit of the decimal mass or mass to charge ratio window preferably increases negatively at a rate of −0.09% times $\Delta M$ below −20 Da (i.e. when $\Delta M$ is −100, then the lower limit of the decimal mass or mass to charge ratio window is set at −20 mDa−0.09%*(100 Da−20 Da)=−20 mDa−0.072 Da=−92 mDa).

It will be appreciated that each different parent drug will have a specific known mass or mass to charge ratio. The approach according to the preferred, embodiment assumes that metabolites of the parent drug will have a similar structure to that of the parent drug and that the decimal part of the accurate mass or mass to charge ratio of each metabolite will be similar to the decimal part of the accurate mass or mass to charge ratio of the parent drug.

Ions which according to the preferred embodiment are determined as having an accurate mass or mass to charge ratio with a decimal part which falls within the decimal mass or mass to charge ratio window as determined by the preferred embodiment are then preferably selected for further analysis by, for example, MS/MS. For example, a mass filter such as a quadrupole mass filter may be used to select specific ions which are considered to be potentially metabolite ions of interest having a specific mass to charge ratio to be onwardly transmitted to a collision or fragmentation cell. The ions are then fragmented within the collision or fragmentation cell and the resulting fragment product ions are mass analysed.

The preferred embodiment enables a large number of endogenous ion peaks that would otherwise have been selected for analysis by MS/MS according to the conventional approach to be automatically eliminated from consideration. This is particularly advantageous and as a result the preferred embodiment relates to a significantly improved method of recognising potential metabolites.

The decimal mass or mass to charge ratio window within which the decimal part of the accurate mass or mass to charge ratio of a metabolite should fail may be defined prior to proceeding with LC-MS and/or LC-MS-MS experiments. The value or size of the decimal mass or mass to charge ratio window may be set to accommodate the mass errors likely to occur during an experimental run. The value or size may also be set according to the elemental composition of the parent drug. For example, if the parent, drug does not contain elements other than carbon, hydrogen, nitrogen, oxygen and fluorine, then the upper and/or lower limits of the decimal mass or mass to charge ratio window may be set to a lower (smaller) value than if the parent drug contains any or all of the elements phosphorous, sulphur and chlorine. This is because phosphorous, sulphur and chlorine all have larger mass deficiencies than carbon, hydrogen, nitrogen, oxygen and fluorine.

The greater the mass or mass to charge ratio difference between that of the parent drug and that of the metabolite, then the more atoms which are likely to be involved in the bio-transformation. Accordingly, if several atoms are considered to be involved in the bio-transformation then greater allowance should preferably be made for the change in the decimal part of the accurate mass or mass to charge ratio. In other words, as the difference in the absolute mass or mass to charge ratio between that, of parent drug and of the metabolite increases, then preferably the width or size of the decimal mass or mass to charge ratio window or the upper and/or lower limits of the decimal mass or mass to charge ratio window should also increase since the metabolite is likely to have a greater mass deficiency or sufficiency.

According to the preferred embodiment allowance may be made for the fact that the maximum change in mass sufficiency that may have occurred in the bio-transformation may be different to the maximum change in mass deficiency which may have occurred. Accordingly, an asymmetric decimal mass or mass to charge ratio window may be used similar, for example, to the asymmetric decimal mass or mass to charge ratio window shown and described in relation to the embodiment depicted in FIG. 2.

According to other less preferred embodiments a simple symmetrical decimal mass or mass to charge ratio window may be used. For example, for mass or mass to charge ratio differences $\Delta M$ between that of parent drug and ions of interest of up to ±20 Da, a decimal mass or mass to charge ratio window having upper and lower limits of ±20 mDa may be used. If the mass or mass to charge ratio difference between that of the parent, drug and the ions of interest is <−20 Da or >20 Da then the upper and lower limits of the decimal mass or mass to charge ratio window may increase at a rate of 0.1% for mass or mass to charge ratio differences <−20 Da or >20 Da.

In the general case, the decimal mass or mass to charge ratio window may have multiple values of decimal mass or mass to charge ratio difference $\delta m$ for a mass or mass to charge ratio difference $\Delta M$ between that of the parent drug ions of interest. The values of $\delta m$ and $\Delta M$ may preferably be defined independently for each polarity of $\delta m$ and $\Delta M$.

According to the preferred embodiment, the mass spectrometer is preferably capable of recording parent ion mass spectra and fragment ion mass spectra from selected precursor or parent ions that are induced to fragment. The mass spectrometer may, for example, comprise a magnetic sector, a Time of Flight, an orthogonal Time of Flight, a quadrupole mass filter, a 3D quadrupole ion trap, a linear quadrupole ion trap or an FT-ICR mass analyser, or any combination thereof.

According to a particularly preferred embodiment, the mass spectrometer may comprise either a magnetic sector, a Time of Flight, an orthogonal Time of Flight or an FT-ICR mass analyser.

The mass spectrometer may according to an embodiment be arranged to default to the acquisition of full parent ion mass spectra unless and until a mass peak is detected wherein the decimal part of the accurate mass or mass to charge ratio of the detected ion falls within a preferably pre-defined decimal mass or mass to charge ratio window. Once such a mass peak is detected then the mass spectrometer and related control software may then preferably switch the instrument so that parent ions having a specific decimal mass or mass to charge ratio or interest are selected and transmitted by a mass filter whilst other ions having decimal masses or mass to charge ratios falling outside the decimal mass or mass to charge ratio window are preferably substantially attenuated or lost to the system. Selected parent ions of interest are then preferably passed to a fragmentation or collision cell which preferably comprises an ion guide and a collision gas maintained at a pressure preferably >10$^{-3}$ mbar. The ions are preferably accelerated into the collision or fragmentation cell at energies such that upon colliding with the collision gas present in the collision or fragmentation cell, the ions are preferably caused to fragment into fragment product ions. The fragment product ions are then preferably mass analysed and a full mass spectrum of the fragment product ions is then preferably obtained.

Although the size of the decimal mass or mass to charge ratio window is preferably pre-defined, according to other less preferred embodiments the size of the decimal mass or mass to charge ratio window may be altered in response to experimental data or on the basis of another parameter. According to an embodiment, for example, a first experimental run may be performed wherein a decimal mass or mass to charge ratio window having a first profile or size as a function of $\Delta M$ may be applied and then in a second subsequent experimental run a decimal mass or mass to charge ratio window having a second different profile or size as a function of $\Delta M$ may be applied.

According to an embodiment control software may select or determine other parameters including the optimum fragmentation collision energy appropriate for a selected precursor or parent ion.

An important advantage of the preferred embodiment is that it enables more useful MS/MS spectra to be acquired within the limited timescale of a single LC-KS experiment. This reduces the time taken to get the required data. Another important advantage of the preferred embodiment is that the preferred method facilitates the detection of low level metabolites that might otherwise be missed, if the conventional approach were adopted, due to the presence of a large number of relatively intense endogenous mass peaks.

Figure 3:
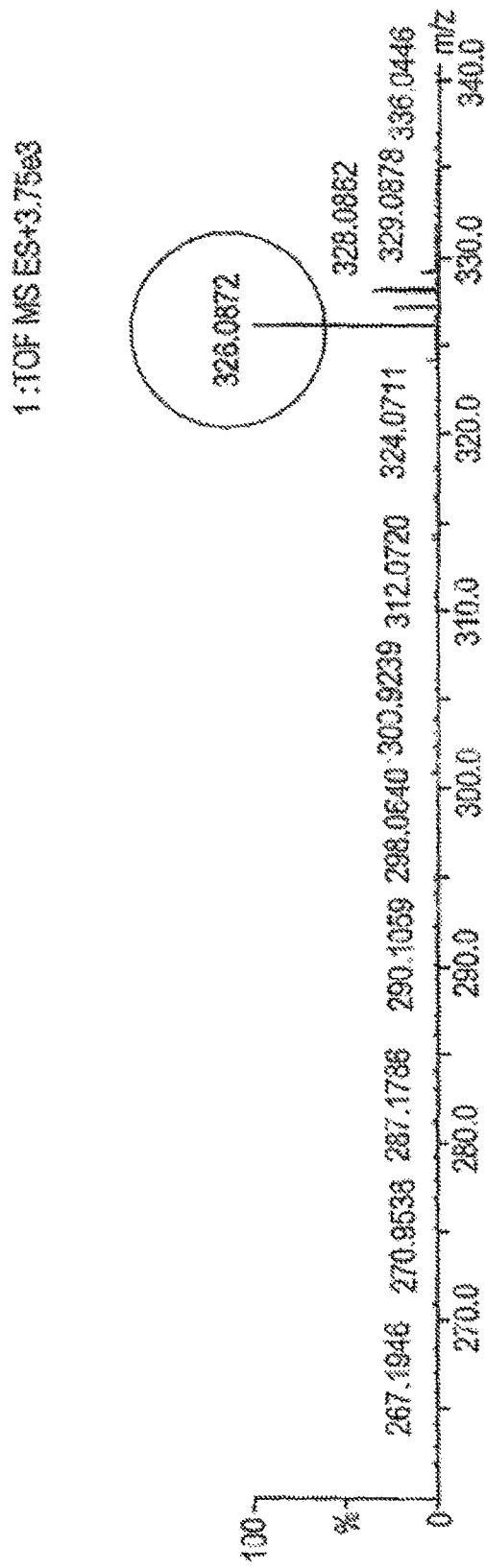
FIG. 3 shows a parent ion mass spectrum of Midazolam.
Figure 4:
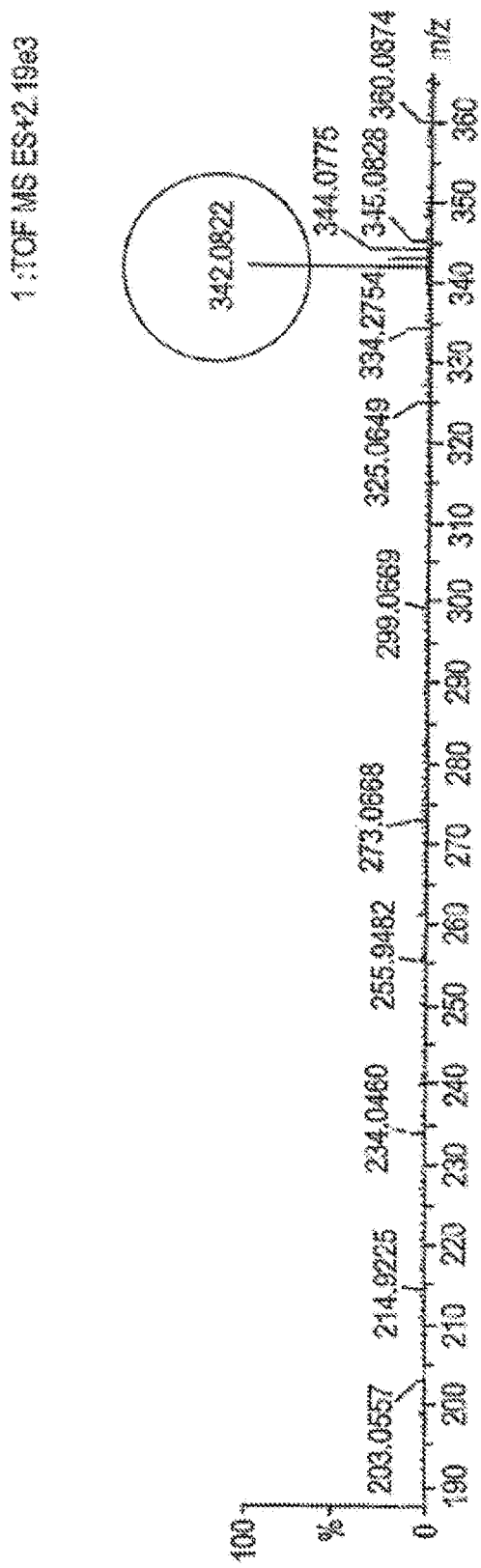
FIG. 4 shows a parent ion mass spectrum of a hydroxylated metabolite of Midazolam.

With reference to the example of Midazolem, FIG. 3 shows a parent ion mass spectrum of the drug Midazolem as recorded using a hybrid quadrupole Time of Flight mass spectrometer. The measured mass to charge ratio for the major isotope was determined as being 326.0872 (cf. a theoretical value of 326.0860). FIG. 4 shows a parent ion mass spectrum of the hydroxylated metabolite of Midazolam as recorded using the same hybrid quadrupole Time of Flight mass spectrometer. The measured mass to charge ratio for the major isotope was determined as being 342.0822 (cf. a theoretical value of 342.0809). From the experimental data, the difference in the decimal part of the accurately determined mass to charge ratio of the parent drug and the decimal part of the accurately determined mass to charge ratio of the hydroxylated metabolite was 0.0872−0.0822=0.0050 Da i.e. a mass deficiency of only 5 mDa.

From the experimental data shown in FIGS. 3 and 4 it will be appreciated that more generally, potential metabolites of Midazolam including the hydroxylated metabolite of Midazolem could be searched for, located and then be selected for further consideration and analysis (preferably by MS-MS). This can be achieved by searching parent ion mass spectral data for mass peaks which may have potentially quite different absolute mass to charge ratios but wherein the difference in the decimal mass or mass to charge ratio of the parent drug and the ion in question is, for example, less than 10 mDa.

The method according to the preferred embodiment provides an effective way of being able to detect efficiently mass peaks likely to be (or at least include) metabolites of interest with no (or relatively few) ions relating to endogenous components also being analysed. The preferred method therefore advantageously effectively filters out or removes from further consideration numerous endogenous mass peaks which would otherwise have been included for consideration according to the conventional techniques.

The preferred embodiment advantageously enables a mass spectrometer to switch to record the fragment ion spectrum of ions which are likely to relate to metabolites of interest within the time scales during which a typical liquid chromatography mass peak is observed without wasting time analysing a large number of ions which turn out not to be metabolites of interest.

According to an embodiment an intelligent exact mass deficiency algorithm may be used together with in silico metabolite prediction to predetermine DDA experiments for metabolism studies preferably using a hybrid quadrupole Time of Flight mass spectrometer.

One of the main problems when carrying out DDA (data dependant experiments) is that a considerable amount of time may be spent performing DDA experiments on ions that turn out not be of interest. As a result, important putative metabolites can easily be missed.

According to an embodiment specific metabolites may be predicted in advance by computer and an appropriate exact decimal mass or mass to charge ratio data filter window may be set. According to the embodiment the metabolites from a given new chemical entity or a standard compound are therefore predicted and then searched for. Once the metabolites have been predicted, an exact decimal mass window may be set so as to only switch to perform, a DDA experiment when ions having decimal masses or mass to charge ratios within the set decimal mass or mass to charge ratio window (which may, for example, have an upper and/or lower limit of 10-20 mDa) are observed as being present.

According to an embodiment potentially unknown metabolites may be discovered. A user may, for example, select or set an exact decimal mass or mass to charge ratio window to detect metabolites already predicted on the basis of their exact decimal mass or mass to charge ratio so that MS/MS experiments maybe carried out. In addition to this, an exact mass deficiency based upon the exact mass or mass to charge ratio of the parent compound can be determined. This particular data filter may be considered more specific than the data filter according to the previously described embodiment since there may be cases where not all of the metabolites will be predicted. Therefore, metabolites which are not predicted will be detected in the DDA experiments with an exact mass or mass to charge ratio data filter.

An exact mass or mass to charge ratio deficiency filter may operate in the following mode. An exact mass or mass to charge ratio deficiency filter based upon the decimal places of the mass or mass to charge ratio of the parent drug under analysis may be used. According to this embodiment a post processing filter may be used that allows the removal of unexpected metabolite entries in a MetaboLynx browser which do not agree with user-defined criteria. The use of this filter can dramatically reduce the number of false entries in an unexpected metabolite table by filtering out the vast majority of matrix-related entries which may share the same nominal mass as potential metabolites. This allows users to use low threshold values during data processing so that very low metabolite levels are identified without going through the tedious task of manually excluding false positives. The filter is preferably an accurate and specific filter since it is based on exact mass and mass deficiencies which are specific to each parent drug of interest.

Each parent drug is comprised of a specific number of elements (C, H, N, O etc). Depending upon the number of each one of the elements mentioned, the decimal mass or mass to charge ratio of the drug will be very specific. For example, with reference to FIG. 5A, Verapamil contains the following elements; C27H38N2O4. This equates to a monoisotopic protonated mass of 455.2910 Da. If an alkyl group is taken away (N-dealkylation, a common metabolic route) and a glucuronide is added, then the mass is shifted by precisely +162.0164 Da. The metabolite therefore has a monoisotopic mass of 617.3074 Da. The decimal mass difference between Verapamil and its N-dealkylated metabolite corresponds with an exact mass deficiency of 0.3074−0.2910=0.0164 Da (16.4 mDa). Therefore, if a decimal mass or mass to charge ratio window of around 20 mDa were used then it would be possible to detect its N-dealkylated glucuronidated metabolite. Prior knowledge of the metabolites of Verapamil may not be necessary if some or all of the following assumptions are made: (i) all metabolites will have decimal masses or mass to charge ratios within 250 mDa of the decimal mass or mass to charge ratio of the corresponding parent; (ii) the metabolites of interest will, in general, have a decimal mass or mass to charge ratio within 100 mDa of the parent if there are no major cleavages leading to much smaller fragments (e.g. the largest, phase II biotransformation, glutathione conjugation, will lead to a mass defect difference of 68 mDa compared to the parent drug); and (iii) most metabolites will fall within a 180 mDa decimal mass or mass to charge ratio window of the parent compound even if certain cleavages take place in the structure to yield smaller fragments.

Figure 5A:
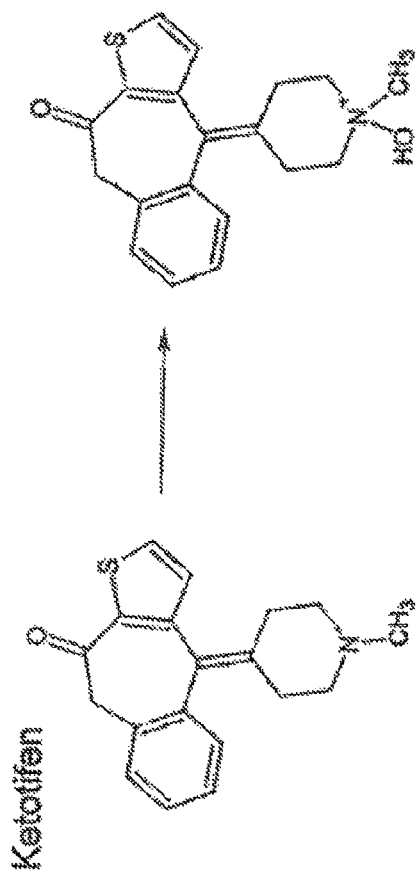
FIG. 5A shows the structure and exact masses of Ketotifen and Verapamil and the structure and exact masses of a metabolite of Ketotifen and Verapamil.
Figure 5A:
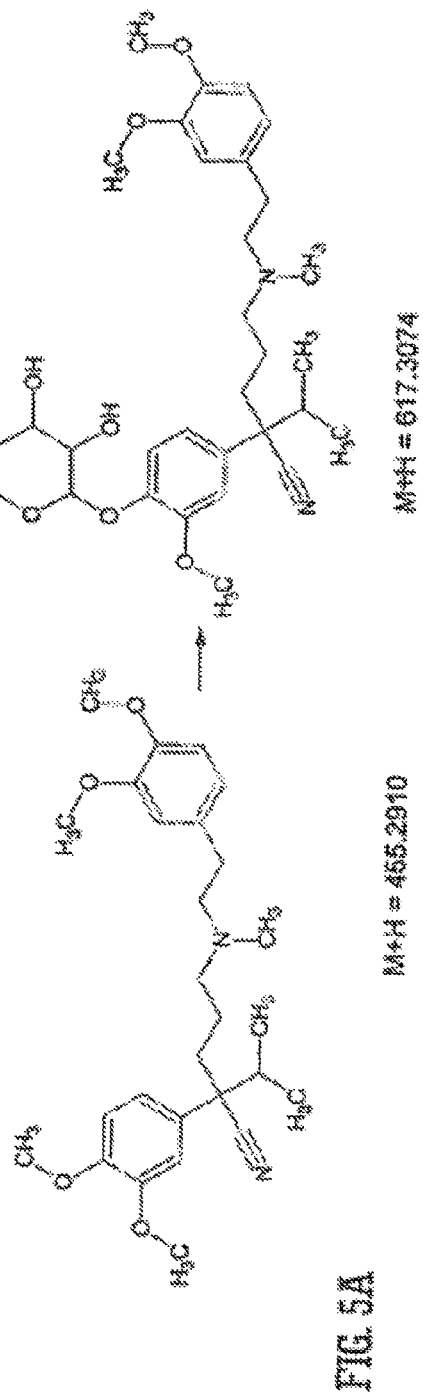
Figure 5B:
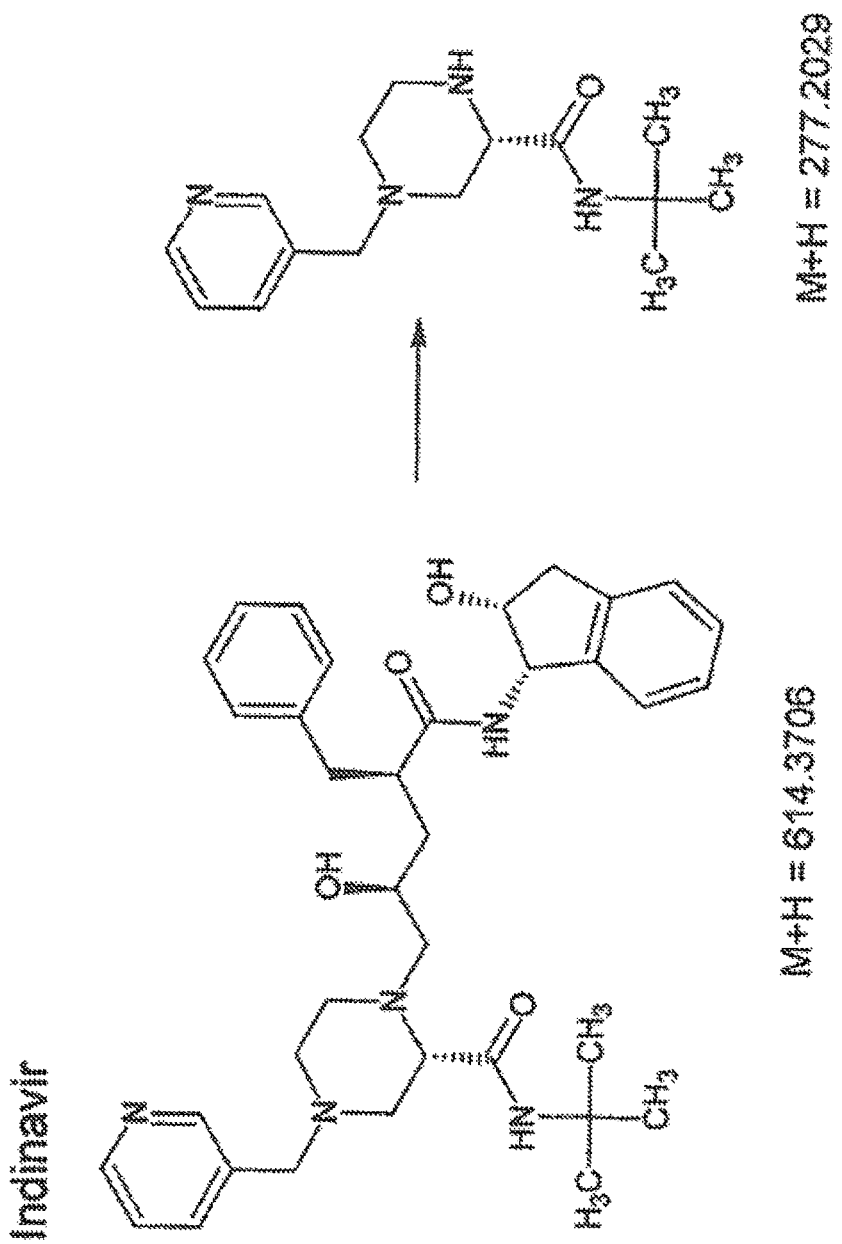
FIG. 5B shows the structure and exact mass of Indinavir and the structure and exact mass of a metabolite of Indinavir.

FIGS. 5A and 5B show a metabolite of Ketotifen, Verapamil and Indinavir and include cleavages. The maximum decimal mass or mass to charge ratio deficiency is in the case of Indinavir (FIG. 5B) wherein the metabolite has a decimal mass or mass to charge ratio which is 167.7 mDa different from the decimal mass or mass to charge ratio of the parent compound. Mass deficiency shifts are very specific for each metabolite and parent drug.

The various embodiments of the present invention may be implemented not only on hybrid quadrupole orthogonal Time of Flight instruments as according to the preferred embodiment, but also using nominal mass instruments such as triple quadrupoles, linear and 3D ion traps and exact mass instruments such as MALDI/Quadrupole Time of Flight and FTMS.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry, conducted with a mass spectrometer including a processing device, the method comprising:
  determining with the mass spectrometer an accurate or exact mass or mass to charge ratio of a first substance or ion, wherein said accurate or exact mass or mass to charge ratio comprises a first integer nominal mass or mass to charge ratio component and a first decimal mass or mass to charge ratio component; and
  searching with the processing device for one or more second substances or ions having a decimal mass or mass to charge ratio component which is between 0 to $x_1$ mDa or milli-mass to charge ratio units greater than said first decimal mass or mass to charge ratio component or between 0 to $x_2$ mDa or milli-mass to charge ratio units lesser than said first decimal mass or mass to charge ratio component, wherein the accurate or exact mass or mass to charge ratio of said first substance or ion minus the accurate or exact mass or mass to charge ratio of a second substance or ion has a value of $\Delta M$ Daltons or mass to charge ratio units, and wherein $x_1$ or $x_2$ varies as a function of $\Delta M$ in a symmetrical manner.

2. A method as claimed in claim 1, wherein said step of searching for one or more second substances or ions comprises searching solely based on the decimal mass or mass to charge ratio component of said one or more second substances or ions and not based on the integer nominal mass or mass to charge ratio component of said one or more second substances or ions.

3. A method as claimed in claim 1, wherein said step of searching for one or more second substances or ions comprises searching some or all second substances or ions which have an integer nominal mass or mass to charge ratio component which is different from said first integer nominal mass or mass to charge ratio component.

4. A method as claimed in claim 1, wherein said first substance or ion comprises or relates to a pharmaceutical compound, drug or active component.

5. A method as claimed in claim 1, wherein said step of searching for one or more second substances or ions further comprises applying a decimal mass or mass to charge ratio window to mass spectral data or a mass spectrum.

6. A method as claimed in claim 5, wherein said decimal mass or mass to charge ratio window filters out, removes, attenuates or at least reduces a significance of second substances or ions having a decimal mass or mass to charge ratio component which falls outside of said decimal mass or mass to charge ratio window.

7. A method of mass spectrometry, conducted with a mass spectrometer including a processing device, the method comprising:
determining with the mass spectrometer an accurate or exact mass or mass to charge ratio of a first substance or ion, wherein said accurate or exact mass or mass to charge ratio comprises a first integer nominal mass or mass to charge ratio component and a first decimal mass or mass to charge ratio component; and
searching with the processing device for one or more second substances or ions having a decimal mass or mass to charge ratio component which is between 0 to $x_1$ mDa or milli-mass to charge ratio units greater than said first decimal mass or mass to charge ratio component or between 0 to $x_2$ mDa or milli-mass to charge ratio units lesser than said first decimal mass or mass to charge ratio component, wherein the accurate or exact mass or mass to charge ratio of said first substance or ion minus the accurate or exact mass or mass to charge ratio of a second substance or ion has a value of $\Delta M$ Daltons or mass to charge ratio units, and wherein $x_1$ or $x_2$ varies as a function of $\Delta M$ in an asymmetrical manner.

8. A method as claimed in claim 1, wherein if $M_{lower} < \Delta M$ or $\Delta M < M_{upper}$ then $x_1$ or $x_2$ has a substantially constant value.

9. A method as claimed in claim 1, wherein if $M_{lower} > \Delta M$ or $\Delta M > M_{upper}$ then $x_1$ or $x_2$ has a substantially non-constant value as a function of $\Delta M$.

10. A method as claimed in claim 9, wherein if $M_{lower} > \Delta M$ or $\Delta M > M_{upper}$ then $x_1$ or $x_2$ varies in a substantially linear manner as a function of $\Delta M$.

11. A method as claimed in claim 8, wherein if $M_{lower} > \Delta M$ or $\Delta M > M_{upper}$ then $x_1$ or $x_2$ varies in a substantially curved, stepped or non-linear manner as a function of $\Delta M$.

12. A method as claimed in claim 1, further comprising selecting for further analysis one or more second substances or ions which have a decimal mass or mass to charge ratio component which is between 0 to $x_1$ mDa or milli-mass to charge ratio units greater than said first decimal mass or mass to charge ratio component or between 0 to $x_2$ mDa or milli-mass to charge ratio units lesser than said first decimal mass or mass to charge ratio component.

13. A method as claimed in claim 12, wherein said step of selecting for further analysis comprises fragmenting said one or more second substances or ions.

14. A method as claimed in claim 12, wherein said step of selecting for further analysis comprises onwardly transmitting one or more second substances or ions which have a decimal mass or mass to charge ratio component which is between 0 to $x_1$ mDa or milli-mass to charge ratio units greater than said first decimal mass or mass to charge ratio component or between 0 to $x_2$ mDa or milli-mass to charge ratio units lesser than said first decimal mass or mass to charge ratio component to a collision or fragmentation cell.

15. A method of mass spectrometry conducted with a mass spectrometer including a processing device, the method comprising:
determining with the mass spectrometer an accurate or exact mass or mass to charge ratio of a parent drug, wherein said accurate or exact mass or mass to charge ratio comprises a first integer nominal mass or mass to charge ratio component and a first decimal mass or mass to charge ratio component; and
searching with the processing device for potential metabolites of said parent drug based on said metabolites having substantially similar decimal mass or mass to charge ratios to that of said parent drug.

16. A method as claimed in claim 15, wherein said step of searching further comprises:
fragmenting ions relating to a potential metabolite of said parent drug so that a plurality of fragment ions are produced; and
mass analysing said fragment ions.

17. A mass spectrometer comprising:
a first device for determining an accurate or exact mass or mass to charge ratio of a first substance or ion, wherein said accurate or exact mass or mass to charge ratio comprises a first integer nominal mass or mass to charge ratio component and a first decimal mass or mass to charge ratio component; and
a second device for searching for one or more second substances or ions having a decimal mass or mass to charge ratio component which is between 0 to $x_1$ mDa or milli-mass to charge ratio units greater than said first decimal mass or mass to charge ratio component or between 0 to $x_2$ mDa or milli-mass to charge ratio units lesser than said first decimal mass or mass to charge ratio component, wherein the accurate or exact mass or mass to charge ratio of said first substance or ion minus the accurate or exact mass or mass to charge ratio of a second substance or ion has a value of $\Delta M$ Daltons or mass to charge ratio units, and wherein $x_1$ or $x_2$ varies as a function of $\Delta M$ in a symmetrical manner.

18. A mass spectrometer comprising:
a first device for determining an accurate or exact mass or mass to charge ratio of a first substance or ion, wherein said accurate or exact mass or mass to charge ratio comprises a first integer nominal mass or mass to charge ratio component and a first decimal mass or mass to charge ratio component; and a second device for searching for one or more second substances or ions having a decimal mass or mass to charge ratio component which is between 0 to $x_1$ mDa or milli-mass to charge ratio units greater than said first decimal mass or mass to charge ratio component or between 0 to $x_2$ mDa or milli-mass to charge ratio units lesser than said first decimal mass or mass to charge ratio component, wherein the accurate or exact mass or mass to charge ratio of said first substance or ion minus the accurate or exact mass or mass to charge ratio of a second substance or ion has a value of $\Delta M$ Daltons or mass to charge ratio units, and wherein $x_1$ or $x_2$ varies as a function of $\Delta M$ in an asymmetrical manner.

* * * * *